US012625059B2

(12) United States Patent
Enoki et al.

(10) Patent No.: US 12,625,059 B2
(45) Date of Patent: May 12, 2026

(54) SNOW ACCRETION TEST METHOD AND SNOW ACCRETION TEST DEVICE

(71) Applicant: ESPEC CORP., Osaka (JP)

(72) Inventors: Hiroyuki Enoki, Osaka (JP); Haruki Seto, Osaka (JP)

(73) Assignee: ESPEC CORP., Osaka (JP)

( * ) Notice: Subject to any disclaimer, the term of this patent is extended or adjusted under 35 U.S.C. 154(b) by 303 days.

(21) Appl. No.: 18/473,869

(22) Filed: Sep. 25, 2023

(65) Prior Publication Data

US 2024/0111073 A1 Apr. 4, 2024

(30) Foreign Application Priority Data

Sep. 30, 2022 (JP) ................................. 2022-157615

(51) Int. Cl.
*G01N 17/00* (2006.01)
*G01N 33/18* (2006.01)
*G01W 1/00* (2006.01)
*F25C 3/04* (2006.01)

(52) U.S. Cl.
CPC ........... *G01N 17/00* (2013.01); *G01N 17/002* (2013.01); *G01W 1/00* (2013.01); *F25C 3/04* (2013.01); *G01N 33/1873* (2024.05)

(58) Field of Classification Search
CPC .. G01N 17/00; G01N 17/002; G01N 33/1873; G01W 1/00; F25C 3/04
See application file for complete search history.

(56) References Cited

FOREIGN PATENT DOCUMENTS

| CN | 114279945 | A | | 4/2022 | |
|---|---|---|---|---|---|
| DE | 102020107425 | A1 | * | 10/2020 | ................ F25C 3/04 |
| FR | 2869050 | A1 | | 10/2005 | |
| JP | H05-113278 | A | | 5/1993 | |
| JP | 2015-187519 | A | | 10/2015 | |
| JP | 2018-036069 | A | | 3/2018 | |
| JP | 2020-134261 | A | | 8/2020 | |
| KR | 102606408 | B1 | * | 11/2023 | .......... G01M 99/008 |
| WO | WO-2014175434 | A1 | * | 10/2014 | ................ F25C 3/04 |

OTHER PUBLICATIONS

The extended European search report issued by the European Patent Office on Jan. 29, 2024, which corresponds to European Patent Application No. 23199304.9-1001 and is related to U.S. Appl. No. 18/473,869.

* cited by examiner

*Primary Examiner* — Jill E Culler
(74) *Attorney, Agent, or Firm* — Studebaker Brackett PLLC

(57) ABSTRACT

In a snow accretion test method, a snow accumulation step of accumulating snow on a specimen, and a snow accretion step of freezing snow accumulated on the specimen in a state where snow is not supplied to the specimen are performed. The snow accumulation step and the snow accretion step are repeatedly performed. In the snow accretion step, the ambient temperature of the specimen is adjusted to a temperature lower than the ambient temperature in the snow accumulation step.

8 Claims, 7 Drawing Sheets

START

SNOW ACCUMULATION
STEP — ST11

SNOW ACCRETION
STEP — ST12

SNOW ACCUMULATION
STEP — ST13

SNOW ACCRETION
STEP — ST14

SNOW ACCRETION TEST METHOD AND SNOW ACCRETION TEST DEVICE

FIELD OF INVENTION

The present invention relates to a snow accretion test method and a snow accretion test device.

BACKGROUND ART

Conventionally, a snow accretion test in which snow is caused to artificially fall and snow is caused to accumulate on a specimen is known. In conducting the snow accretion test, for example, a snow cannon disclosed in JP H5-113278 A can be used. That is, it is possible to forcibly cool the inside of a test chamber to −3° C. or lower, and to spray water in this state to cause snow to fall and accumulate on the specimen.

However, only by simply causing snow to accumulate on the specimen, the resultant snow accumulation situation may be different from the snow accumulation situation obtained in a natural environment. That is, when snow accumulates on an object placed in a natural environment, snow may firmly adhere to the object. On the other hand, when snow is simply caused to fall in the test chamber, even if snow accumulates on the specimen, the snow can be easily scraped off. Therefore, it is difficult to say that the snow accretion situation occurring in the natural environment can be reproduced.

SUMMARY OF THE INVENTION

An object of the present invention is to make it possible to reproduce a snow accretion situation in a more natural environment.

A snow accretion test method according to the present invention includes: a snow accumulation step of accumulating snow on a specimen; and a snow accretion step of freezing snow accumulated on the specimen in a state where snow is not supplied to the specimen, the snow accretion step at least including a period in which an ambient temperature of the specimen is adjusted to a negative temperature.

A snow accretion test device according to the present invention is a snow accretion test device that is capable of carrying out the snow accretion test method, the snow accretion test device including: a test chamber for providing a snowfall environment; an air conditioner for air-conditioning an inside of the test chamber; a nozzle for spraying water particles for obtaining the snowfall environment in the test chamber; and a controller for controlling the air conditioner so that a temperature in the test chamber becomes a temperature set as a temperature for the snow accumulation step and a temperature for the snow accretion step, and activating the nozzle.

BRIEF DESCRIPTION OF THE DRAWINGS

FIG. 6 is a view schematically illustrating a modification of the snow accretion test device for carrying out the snow accretion test method according to the second embodiment.

FIG. 7 is a view schematically illustrating a snow accretion test device for carrying out a snow accretion test method according to a third embodiment.

DETAILED DESCRIPTION

Embodiments for carrying out the present invention will be described below in detail with reference to the drawings.

First Embodiment

Figure 1:
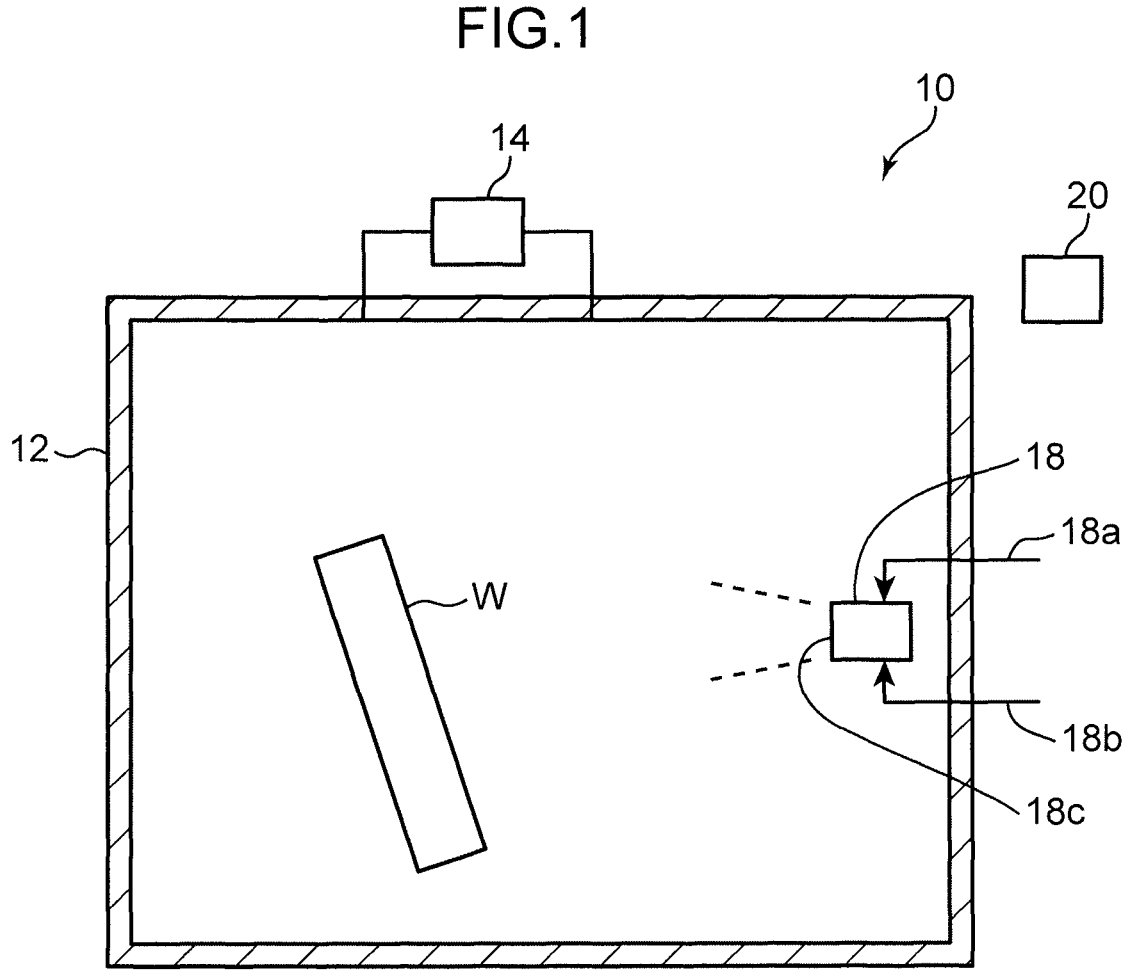
FIG. 1 is a view schematically illustrating a snow accretion test device for carrying out a snow accretion test method according to a first embodiment.

FIG. 1 illustrates a snow accretion test device 10 that can carry out the snow accretion test method according to the present embodiment. The snow accretion test device 10 includes a test chamber 12 for providing a snowfall environment, an air conditioner 14 for air-conditioning the inside of the test chamber 12, a nozzle 18 arranged in the test chamber 12, and a controller 20 that controls the air conditioner 14 and the nozzle 18. The snowfall environment mentioned here is a temperature environment in which snow can be formed from water droplets, and means a temperature environment of −1° C. or lower, for example. The air conditioner 14 is configured to be able to adjust the air temperature in the test chamber 12 to a temperature suitable for the snowfall environment.

The nozzle (spray nozzle) 18 is configured to spray fine water particles. For example, the nozzle 18 is configured by a two-fluid nozzle, and is configured to spray air and fine water particles (extremely fine water droplets). The nozzle 18 is connected with an air supply path 18a and a cold water supply path 18b. The nozzle 18 sprays compressed air (or cooled compressed air) supplied through the air supply path 18a and cold water supplied through the cold water supply path 18b from a spray port 18c. In the spray port 18c, the compressed air and the cold water collide with each other, whereby the cold water is crushed. Therefore, a fluid in a state where air and fine water particles are mixed is sprayed from the spray port 18c. The water particles sprayed from the spray port 18c turn into snow in the test chamber 12. In the illustrated example, since the nozzle 18 sprays air and water particles horizontally, snow adheres to a specimen W from the side. However, the present embodiment is not limited to this, and the nozzle 18 may be arranged such that snow adheres to the specimen W from above, for example. The nozzle 18 is not limited to be configured by a two-fluid nozzle, and may be configured by a one-fluid nozzle.

The controller 20 controls the air conditioner 14 and the nozzle 18 so as to perform a snow accumulation step and a snow accretion step described later for a predetermined time set respectively. That is, in the snow accumulation step performed for a predetermined time, the controller 20 controls the air conditioner 14 so that the temperature in the test chamber 12 becomes a temperature set as a temperature suitable for the snowfall environment. The controller 20 activates the nozzle 18 so that air and water particles are sprayed from the nozzle 18 in the snow accumulation step. In the snow accretion step performed for a predetermined time, the controller 20 controls the air conditioner 14 so that the temperature becomes a temperature set as a temperature lower than the temperature in the test chamber 12 in the snow accumulation step. The controller 20 controls the nozzle 18 so that air and water particles are not sprayed in the snow accretion step.

The time for performing the snow accumulation step and the snow accretion step may be a time set in the controller 20 by a worker inputting the time using a setter not illustrated, or may be a time not input by the worker but automatically set by the controller 20. The temperature in the test chamber 12 in the snow accumulation step and the snow accretion step may also be a temperature set in the controller 20 by the worker inputting the temperature using the setter not illustrated, or may be a temperature not input by the worker but automatically set by the controller 20. For example, the controller 20 can automatically set the temperature of the snow accretion step so that the temperature becomes lower than the temperature in the test chamber 12 in the snow accumulation step by a predetermined temperature (e.g., 3° C.).

Figure 2:
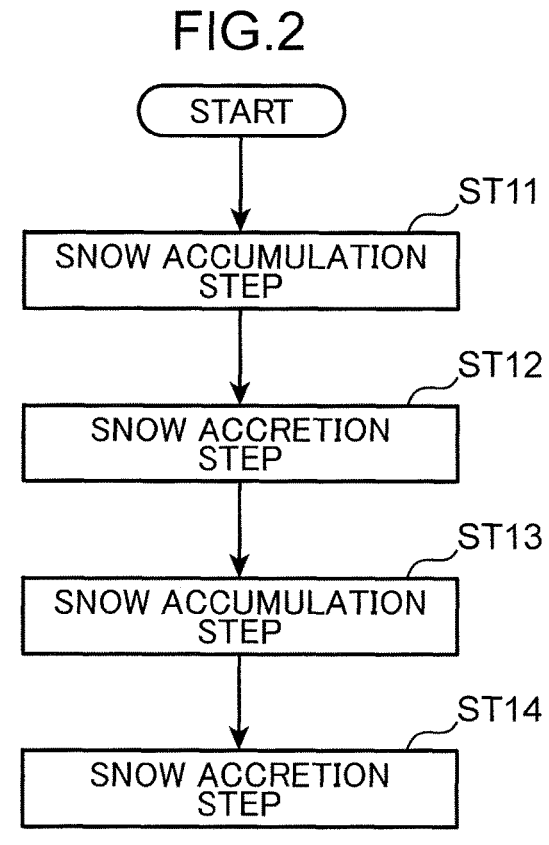
FIG. 2 is a view for describing the snow accretion test method according to the first embodiment.
Figure 3:
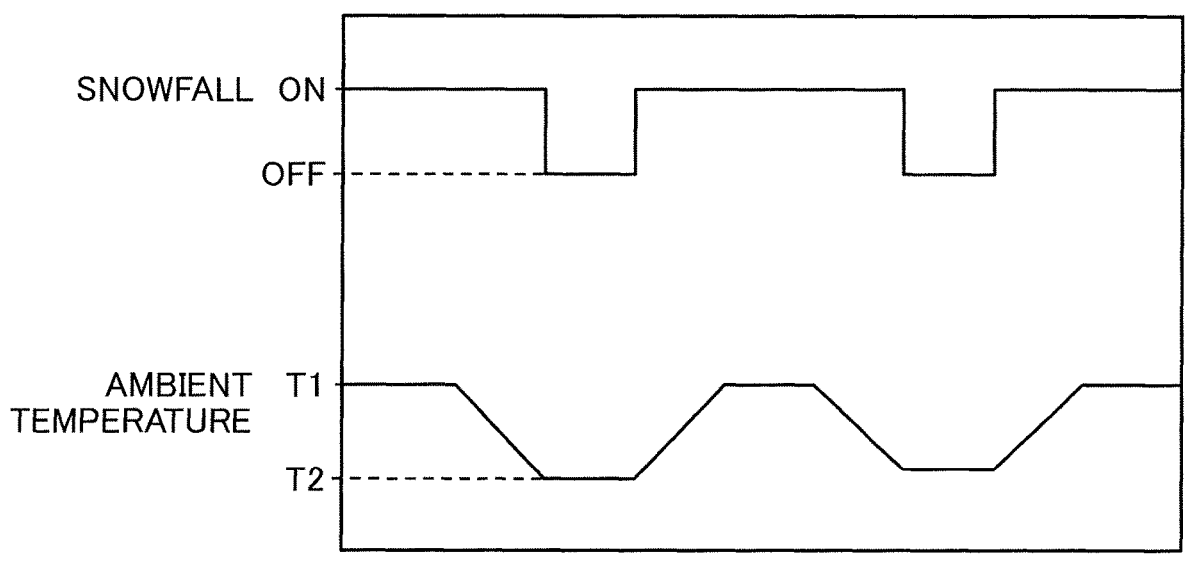
FIG. 3 is a view for describing the presence or absence of snowfall and a change in a specimen ambient temperature in each step in the snow accretion test method.

In the snow accretion test method according to the present embodiment, as illustrated in FIGS. 2 and 3, the snow accumulation step and the snow accretion step are alternately and repeatedly performed. Specifically, in a first snow accumulation step (step ST11), the controller 20 controls the air conditioner 14 so that the inside of the test chamber 12 becomes a temperature (temperature T1) set as a temperature suitable for the snowfall environment. Then, in this snow accumulation step, in a state where the specimen W is arranged in the test chamber 12, a fluid in a state where air and fine water particles are mixed is sprayed from the nozzle 18 ("snowfall ON" in FIG. 3). The temperature in the test chamber 12 at this time, that is, the ambient temperature of the specimen W is a temperature (temperature T1) of –1° C. or lower. Since the temperature in the test chamber 12 is –1° C. or lower, the water particles sprayed from the nozzle 18 turn into snow while drifting in the test chamber 12. Since this snow accumulates on the specimen W, the snow accumulation thickness gradually increases on the specimen W.

When the first snow accumulation step is performed for a preset time, the step proceeds to a first snow accretion step (step ST12). In the first snow accretion step, the spray of air and water particles by the nozzle 18 is stopped ("snowfall OFF" in FIG. 3). Therefore, in the first snow accretion step, snow is not supplied to the specimen W. Therefore, the snow accumulation amount on the specimen W is maintained. In the first snow accretion step, the controller 20 controls the air conditioner 14 so that the temperature in the test chamber 12 (the ambient temperature of the specimen W) becomes a temperature (temperature T2) lower than the temperature T1. For example, the temperature T2 is a temperature of –5° C. or lower. That is, the snow accumulation step reproduces a state where snow is caused to fall in the daytime in a cold region, and the snow accretion step reproduces a state where accumulated snow freezes at night in a cold region. The timing of lowering the temperature in the test chamber 12 may be coincided with the snow supply stoppage, and the temperature may be started to be lowered before the spray from the nozzle 18 is stopped, or the temperature may be started to be lowered after the spray is stopped.

The snow accumulated on the specimen W contains moisture. Moreover, since snow is not supplied to the specimen W in the snow accretion step, snow does not newly accumulate. Therefore, in the snow accretion step, the snow accumulated on the specimen W is efficiently frozen by lowering the temperature in the test chamber 12. That is, on the specimen W, snowflakes including snowflakes on the surface of a snow accumulation layer are efficiently bonded to each other.

When the first snow accretion step is performed for a preset time, a second snow accumulation step is performed (step ST13). Since the second snow accumulation step is performed under the same conditions as the first snow accumulation step, the temperature in the test chamber 12 is adjusted to the temperature T1 again. That is, the controller 20 controls the air conditioner 14 so that the temperature in the test chamber 12 becomes higher than the temperature in the test chamber 12 in the first snow accretion step. Since the controller 20 activates the nozzle 18, a fluid in a state where air and fine water particles are mixed is sprayed from the nozzle 18. Due to this, snow further accumulates on the snow solidified on the specimen W in the first snow accretion step.

Then, when the second snow accumulation step is performed for a preset time, a second snow accretion step is performed (step ST14). The second snow accretion step is a step in which the same control as the first snow accretion step is performed. Therefore, the spray of air and water particles from the nozzle 18 is stopped, and the temperature in the test chamber 12 is adjusted to the temperature T2 again. Thereby, the snow accumulation layer grown in the second snow accumulation step can be frozen.

Hereinafter, the snow accumulation step and the snow accretion step are repeatedly performed a predetermined number of times. This enables a thick layer of snow to be formed on the specimen W.

As described above, in the present embodiment, after the snow accumulation step of accumulating snow on the specimen W is performed, the snow accretion step for freezing the snow accumulated on the specimen W is performed. In this snow accretion step, moisture of snow on the specimen W is frozen in a state where the specimen W is not supplied with snow. Therefore, snowflakes can be bonded to each other on the specimen W. Since snow firmly adheres also to the specimen W, snow accumulated on the specimen W can be brought into a state of not being easily removable by hand. Therefore, it is possible to reproduce a situation in nature where accumulated snow hardens at night and firmly adheres to an object on which the snow has accumulated.

Moreover, in the present embodiment, since the snow accumulation step and the snow accretion step are repeatedly performed, the layer of snow can be grown so that the snow that accumulates on the specimen W becomes thick. That is, when only the snow accumulation step is performed for a long time, the accumulated snow does not necessarily freeze. Therefore, snow accumulation collapses due to the weight of snow, and a thick layer of snow cannot be formed on the specimen W. On the other hand, by performing the snow accretion step between the snow accumulation step and the snow accumulation step, it is possible to solidify snow, and it is possible to grow a layer of snow.

In the present embodiment, in the snow accretion step, the ambient temperature of the specimen W is adjusted to a temperature lower than the ambient temperature in the snow accumulation step. Therefore, it is possible to promote freezing of snow in the snow accretion step. In particular, in the present embodiment, since the snow accumulation step and the snow accretion step are repeatedly performed, in the snow accumulation step after snow freezes in the snow accretion step, the ambient temperature of the specimen W is adjusted to a temperature higher than the ambient temperature of the specimen W during the snow accretion step. Therefore, wet snow can be further accumulated on the accumulated layer of snow in the snow accumulation step. This can make it easy to freeze snow in the subsequent snow accretion step.

In the present embodiment, the temperature of the test chamber 12 in the snow accretion step is adjusted to be lower than the temperature of the test chamber 12 in the snow accumulation step, but the present invention is not limited to this. For example, the temperature of the test chamber 12 may be set to the same temperature in the snow accretion step and the snow accumulation step. However, by setting the temperature of the test chamber 12 in the snow accretion step lower than the temperature of the test chamber 12 in the snow accumulation step, it is possible to efficiently solidify the snow accumulated on the specimen W.

In the present embodiment, the snow accumulation step and the snow accretion step are performed a plurality of times, but the present invention is not limited to this. The snow accumulation step and the snow accretion step may each be performed only once. Even in this case, in the snow accretion step, since the snowflakes can be bonded to each other on the specimen W, the snow can be caused to firmly adhere to the specimen W.

Figure 4:
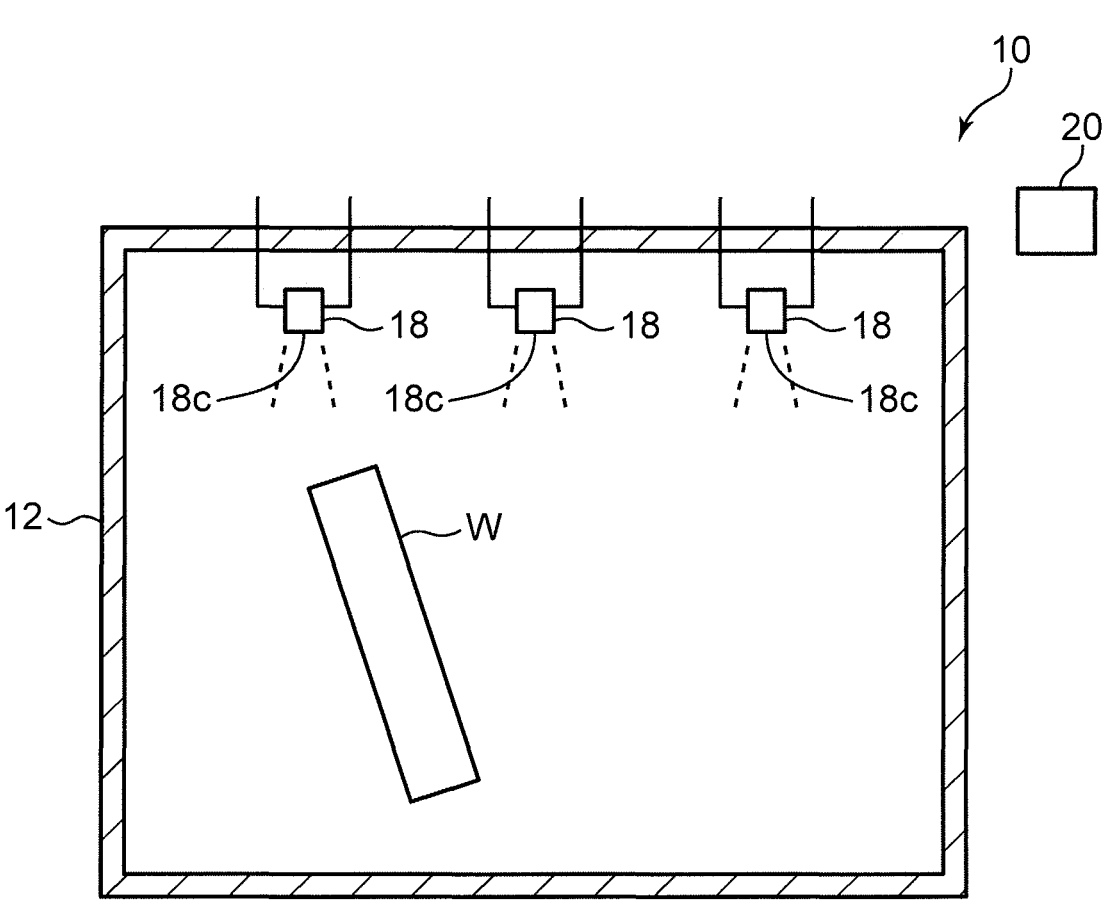
FIG. 4 is a view schematically illustrating a modification of the snow accretion test device for carrying out the snow accretion test method according to the first embodiment.

In the present embodiment, the nozzle 18 of the snow accretion test device 10 is configured to horizontally spray fine water particles toward the specimen W, but the present embodiment is not limited to this. For example, as illustrated in FIG. 4, the nozzle 18 may be configured to be arranged downward in the test chamber 12 to cause water fine particles to fall.

Second Embodiment

Figure 5:
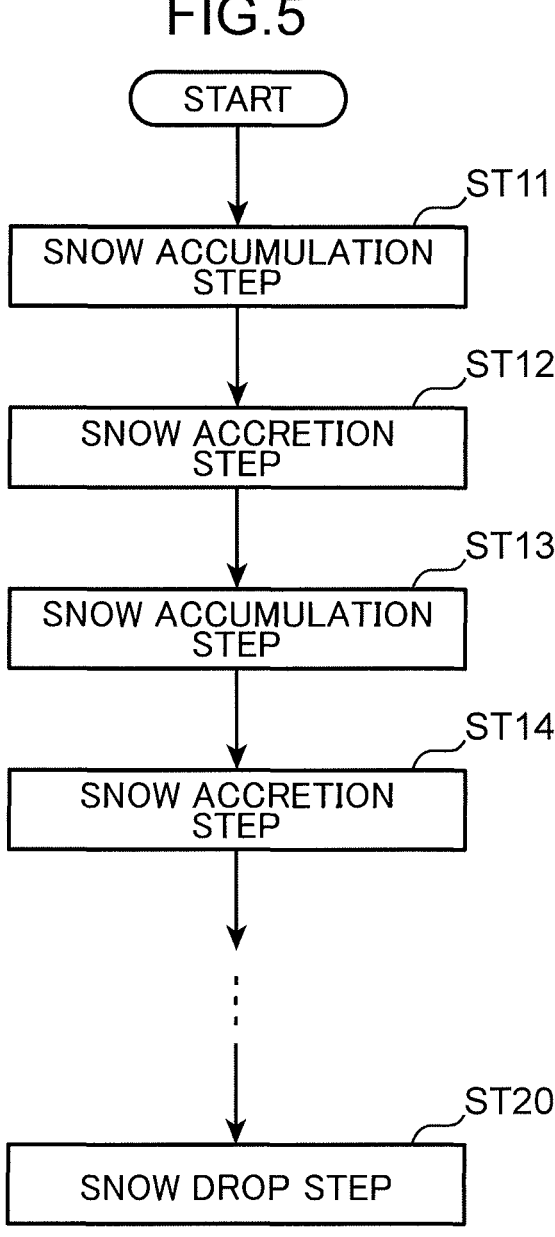
FIG. 5 is a view for describing the snow accretion test method according to a second embodiment.

As illustrated in FIG. 5, in the second embodiment, a snow drop step is performed. Here, the same components as those in the first embodiment are given the same reference numerals, and a detailed description thereof will be omitted.

In the second embodiment, after the snow accumulation step and the snow accretion step are performed at least once, a snow drop step for melting at least a part of the snow accumulated on the specimen W and causing snow to drop from the specimen W is performed (step ST20). The snow drop step is implemented by control by the controller 20. In the snow drop step, the controller 20 controls the air conditioner 14 so that the temperature in the test chamber 12 (the ambient temperature of the specimen W) is higher than the temperature in the snow accumulation step. For example, the temperature of the test chamber 12 in the snow drop step is set to +5 to 25° C., which is higher than the temperature in the test chamber 12 in the snow accretion step. The snow drop step may be continued for a predetermined time, or may be performed until it is confirmed that the accumulated snow collapses. In the snow drop step, the nozzle 18 is stopped. Therefore, air and water particles are not sprayed from the nozzle 18.

In a case where the snow drop step is performed for a predetermined time, this duration time may be a time set in the controller 20 by the worker inputting the time using the setter not illustrated, or may be a time not input by the worker but automatically set by the controller 20. The temperature in the test chamber 12 in the snow drop step may also be a temperature set in the controller 20 by the worker inputting the temperature using the setter not illustrated, or may be a temperature not input by the worker but automatically set by the controller 20. For example, the controller 20 can automatically set the temperature in the test chamber 12 in the snow drop step to a temperature higher than the temperature in the test chamber 12 in the snow accumulation step or the snow accretion step by a predetermined temperature (e.g., 30° C.).

Figure 6:
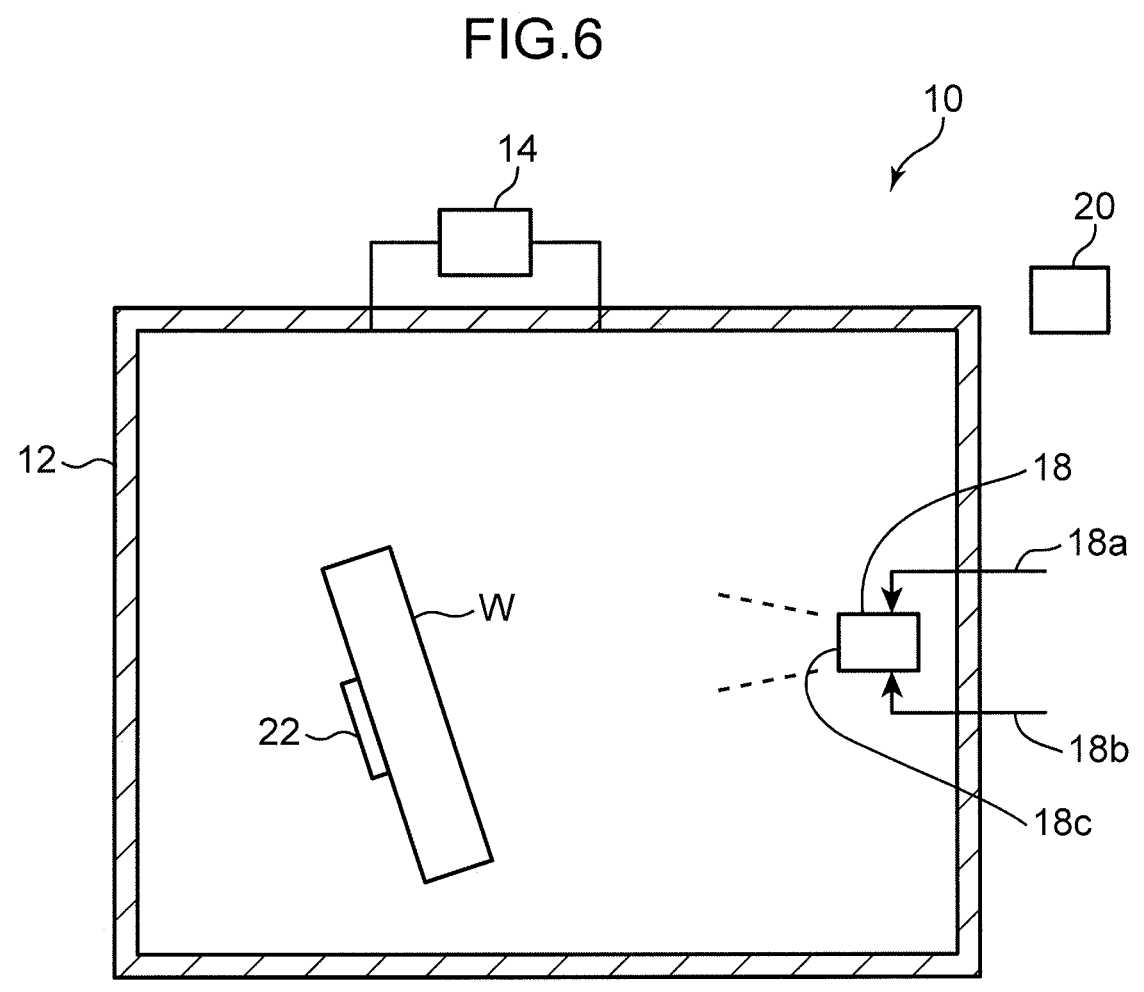

The snow drop step is not limited to raising the temperature in the test chamber 12. For example, the temperature of the specimen W may be raised. In this case, in order to raise the temperature of the specimen W, as illustrated in FIG. 6, a heater 22 that heats the specimen W may be attached to the specimen W. Alternatively, hot air may be blown onto the specimen W. The temperature of the specimen W in the snow drop step in this case only needs to be a positive temperature. When the specimen W is something that generates heat by being energized, the specimen W may be energized so that the specimen W self-generates heat.

According to the present embodiment, it is possible to reproduce a phenomenon of dropping snow accumulated on an object.

Although descriptions of other configurations, operations, and effects are omitted, the description of the first embodiment can be applied to the description of the second embodiment.

Third Embodiment

Figure 7:
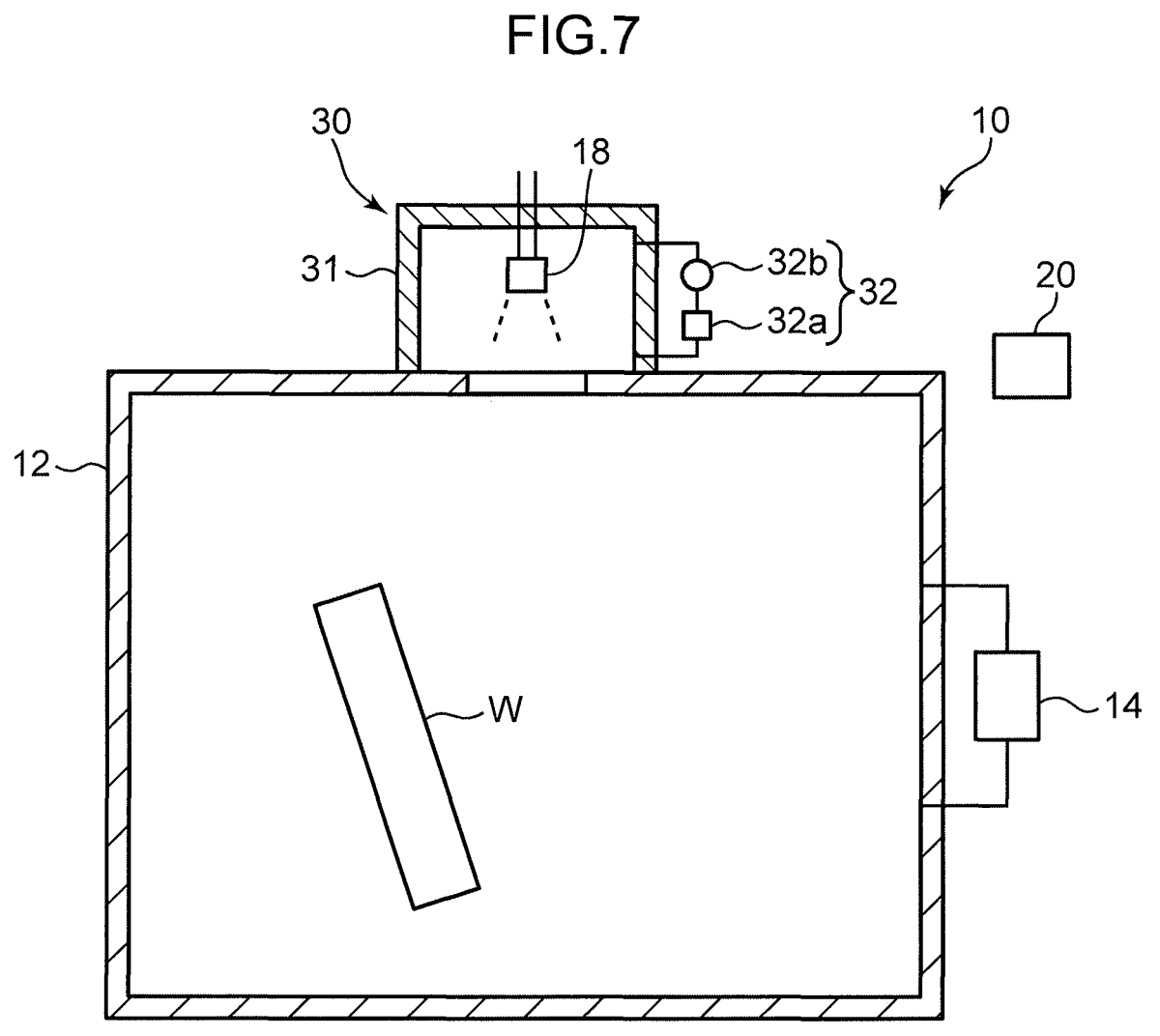

FIG. 7 illustrates the snow accretion test device 10 for carrying out the snow accretion test method according to the third embodiment. Here, the same components as those in the first and second embodiments are given the same reference numerals, and a detailed description thereof will be omitted.

This snow accretion test device 10 is provided with a snowmaking device 30 for making snow. The snowmaking device 30 includes a snowmaking chamber 31 adjacent to the test chamber 12 and the nozzle 18 arranged in the snowmaking chamber 31. The snowmaking chamber 31 is a chamber that provides a temperature environment lower than that of the test chamber 12, and generates snow from fine water particles sprayed from the nozzle 18 in the snowmaking chamber 31.

The inside of the snowmaking chamber 31 is adjusted to a temperature environment of −10° C. or lower by the controller 20, for example. Therefore, the snowmaking chamber 31 is provided with a snowmaking air conditioner 32 including a cooler 32a that cools the air in the snowmaking chamber 31 and a blower 32b that blows out the air cooled by the cooler 32a into the snowmaking chamber 31. That is, the controller 20 is configured to control the snowmaking air conditioner 32.

In this snow accretion test device 10, since the snowmaking chamber 31 and the test chamber 12 are separated, it is not necessary to set the temperature in the test chamber 12 (the ambient temperature of the specimen W) to a negative temperature range. Therefore, the temperature in the test chamber 12 (the ambient temperature of the specimen W) in the snow accumulation step only needs to be set to +5° C. or lower. That is, since the temperature in the test chamber 12 can be set to a higher state as compared with the first embodiment, snowfall in a region other than a cold region can be reproduced. On the other hand, the temperature in the test chamber 12 (the ambient temperature of the specimen W) in the snow accretion step is set to −1° C. or lower. That is, in the snow accretion step, similarly to the first embodiment, the temperature is set to a negative temperature range in order to freeze the accumulated snow. Thus, the temperature in the test chamber 12 (the ambient temperature of the specimen W) in the snow accretion step is set lower than the temperature in the test chamber 12 in the snow accumulation step. The temperature in the test chamber 12 in the snow accumulation step and the snow accretion step may also be a temperature set in the controller 20 by the worker inputting the temperature using the setter not illustrated, or may be a temperature not input by the worker but automatically set by the controller 20. For example, the controller 20 can automatically set the temperature in the test chamber 12 in the snow accretion step to a temperature lower than the temperature in the test chamber 12 in the snow accumulation step by a predetermined temperature.

The timing of lowering the temperature in the test chamber 12 may be coincided with the snow supply stoppage, and the temperature may be started to be lowered before the spray from the nozzle 18 is stopped, or the temperature may be started to be lowered after the spray is stopped. That is, the snow accretion step only needs to include at least a period in which the ambient temperature of the specimen W is adjusted to a negative temperature.

Even when the snowmaking device 30 is provided, the temperature in the test chamber 12 (the ambient temperature of the specimen W) in the snow accumulation step may be set to a negative temperature range. In this case, the temperature in the test chamber 12 (the ambient temperature of the specimen W) may be the same temperature in the snow accumulation step and the snow accretion step.

The third embodiment is the same as the first embodiment except that the temperature in the test chamber 12 (the ambient temperature of the specimen W) is different from that of the first embodiment. Therefore, the snow accumulation step and the snow accretion step may be repeatedly performed, or may each be performed only once. Similarly to the second embodiment, the snow drop step (step ST20) may be performed.

Although descriptions of other configurations, operations, and effects are omitted, the descriptions of the first and second embodiments can be applied to the description of the third embodiment.

Fourth Embodiment

Figure 8:
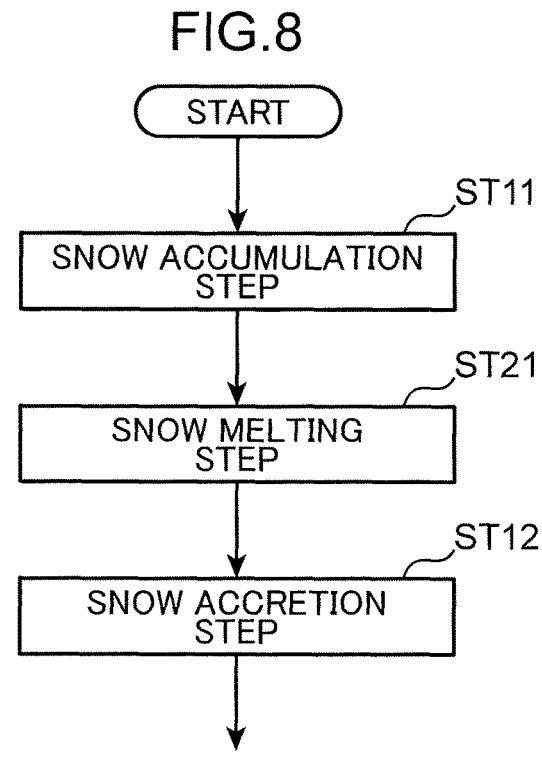
FIG. 8 is a view for describing the snow accretion test method according to a fourth embodiment.

In the fourth embodiment, as illustrated in FIG. 8, before the snow accretion step is performed, a snow melting step (step ST21) of melting snow accumulated on the specimen W is performed. Here, the same components as those in the first, second, and third embodiments are given the same reference numerals, and a detailed description thereof will be omitted.

Figure 9:
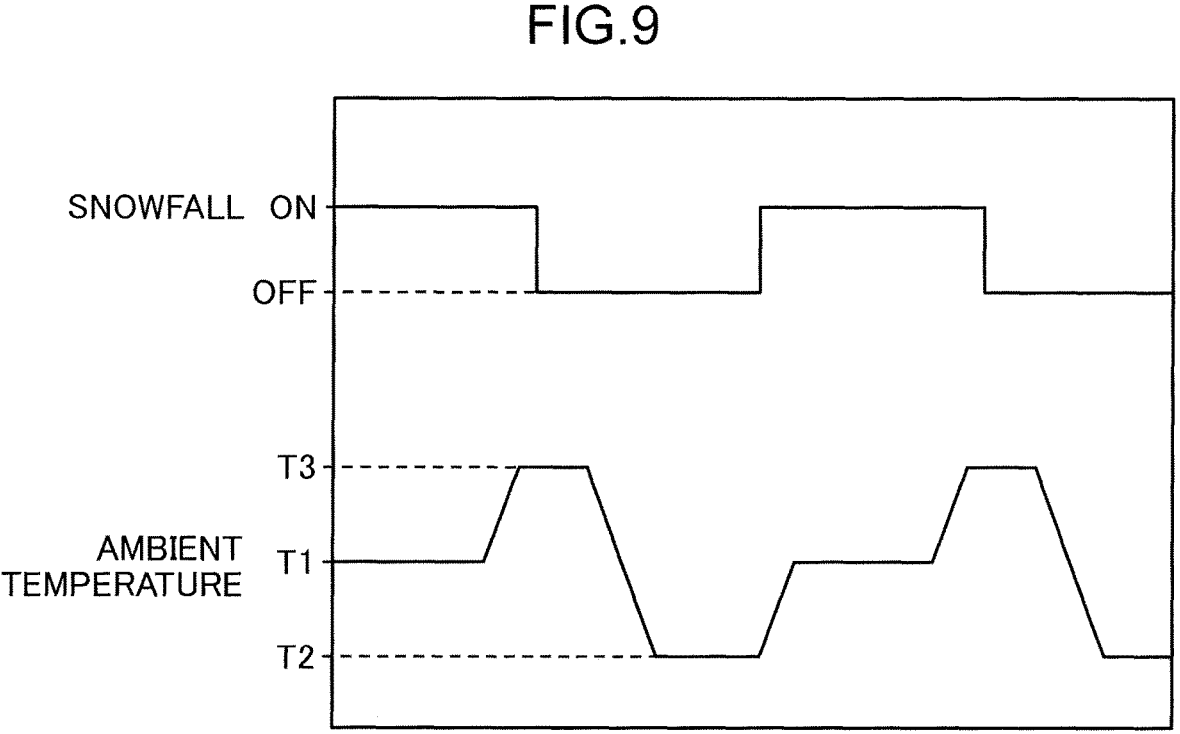
FIG. 9 is a view for describing the presence or absence of snowfall and a change in the specimen ambient temperature in each step in the snow accretion test method.

The snow melting step is a step performed following the snow accumulation step. In this snow melting step, supply of snow to the specimen W is stopped, and the temperature in the test chamber 12 is set to a temperature higher than the temperature in the test chamber 12 (the ambient temperature of the specimen W) in the snow accumulation step. For example, the temperature in the test chamber 12 in the snow melting step is set to a positive temperature range. Therefore, as illustrated in FIG. 9, when the snow accumulation step (step ST11) is performed for a predetermined time, the temperature of the test chamber 12 is raised from the temperature T1 to a temperature T3, and spray of water particles from the nozzle 18 is stopped. Therefore, even if dry snow accumulates on the specimen W in the snow accumulation step, a part of the accumulated snow can be melted, and wet snow can be brought into a state of being accumulated. Then, when the snow melting step is performed for a predetermined time, the step proceeds to the snow accretion step (step ST12).

The time for performing the snow melting step may be a time set in the controller 20 by the worker inputting the time using the setter not illustrated, or may be a time not input by the worker but automatically set by the controller 20. The temperature in the test chamber 12 in the snow melting step may also be a temperature set in the controller 20 by the worker inputting the temperature using the setter not illustrated, or may be a temperature not input by the worker but automatically set by the controller 20. For example, the controller 20 can automatically set the temperature in the test chamber 12 in the snow melting step to a temperature higher than the temperature of the test chamber 12 in the snow accumulation step or the snow accretion step by a predetermined temperature and in a positive temperature range.

In the present embodiment, since the snow melting step is performed, even when dry snow is caused to fall in the snow accumulation step, wet snow can be brought into a state of being accumulated on the specimen W in a stage before the snow accretion step. Therefore, snow can be easily frozen in the snow accretion step without being restricted by the snow quality in the snow accumulation step. In a case where the accumulated snow in the snow accretion step is wet snow, the accumulated snow becomes firmer than a case where dry snow is accumulated.

Although descriptions of other configurations, operations, and effects are omitted, the descriptions of the first to third embodiments can be applied to the description of the fourth embodiment.

Other Embodiments

The embodiments disclosed here should be considered illustrative in all respects and not restrictive. The present invention is not limited to the above-described embodiments, and various changes, improvements, and the like can be made without departing from the scope thereof. In the above-described embodiments, the snow accretion test device 10 adjusts the temperature in the entire test chamber 12 as the ambient temperature of the specimen W, but the present invention is not limited to the method of adjusting the temperature in the entire test chamber 12. For example, the snow accretion test device 10 may include a local cooling device or a local heating device such as a spot cooler or a spot heater, and the controller 20 may control this local cooling device or the local heating device to locally adjust the ambient temperature of the specimen W.

The above-described embodiments will now be outlined.

(1) A snow accretion test method according to the above-described embodiments performs: a snow accumulation step of accumulating snow on a specimen; and a snow accretion step of freezing snow accumulated on the specimen in a state where snow is not supplied to the specimen, the snow accretion step at least including a period in which an ambient temperature of the specimen is adjusted to a negative temperature.

In the snow accretion test method, after the snow accumulation step of accumulating snow on the specimen is performed, the snow accretion step for freezing the snow accumulated on the specimen is performed. In this snow accretion step, since moisture of snow is frozen in a state where the specimen is not supplied with snow, snowflakes can be bonded to each other on the specimen. Since snow firmly adheres also to the specimen, snow accumulated on the specimen can be brought into a state of not being easily removable by hand. Therefore, it is possible to reproduce a situation in nature where accumulated snow hardens at night and firmly adheres to an object on which the snow has accumulated.

(2) The snow accumulation step and the snow accretion step may be repeatedly performed. In this aspect, the layer of snow can be grown so that the snow that accumulates on the specimen becomes thick. That is, when only the snow accumulation step is performed for a long time, the accumulated snow does not necessarily freeze. Therefore, snow accumulation collapses due to the weight of snow, and a thick layer of snow cannot be formed on the specimen. On the other hand, by performing the snow accretion step between the snow accumulation step and the snow accumulation step, it is possible to solidify snow, and it is possible to grow a layer of snow.

(3) In the snow accretion step, the ambient temperature of the specimen may be adjusted to a temperature lower than the ambient temperature in the snow accumulation step. In this aspect, it is possible to promote freezing of snow in the snow accretion step. In particular, when the snow accumulation step and the snow accretion step are repeatedly performed, in the snow accumulation step after snow freezes in the snow accretion step, the ambient temperature of the specimen is adjusted to a temperature higher than the ambient temperature of the specimen during the snow accretion step. Therefore, wet snow can be further accumulated on the accumulated layer of snow in the snow accumulation step. This can make it easy to freeze snow in the subsequent snow accretion step.

(4) In the snow accretion test method, the snow drop step of raising the ambient temperature of the specimen or the specimen temperature so that snow accumulated on the specimen drops from the specimen may be performed. In this aspect, it is possible to reproduce a phenomenon of dropping snow accumulated on an object.

(5) In the snow accretion test method, before the snow accretion step is performed, the snow melting step of melting snow accumulated on the specimen may be performed. In this aspect, since the snow melting step is performed, even when dry snow is caused to fall in the snow accumulation step, wet snow can be brought into a state of being accumulated in a stage before the snow accretion step. Therefore, snow can be easily frozen in the snow accretion step without being restricted by the snow quality in the snow accumulation step.

(6) A snow accretion test device according to the above-described embodiments is a snow accretion test device that is capable of carrying out the snow accretion test method, the snow accretion test device including: a test chamber for providing a snowfall environment; an air conditioner for air-conditioning an inside of the test chamber; a nozzle for spraying water particles for obtaining the snowfall environment in the test chamber; and a controller for controlling the air conditioner so that a temperature in the test chamber becomes a temperature set as a temperature for the snow accumulation step and a temperature for the snow accretion step, and activating the nozzle.

As described above, it is possible to reproduce a snow accretion situation in a more natural environment.

This application is based on Japanese Patent application No. 2022-157615 filed in Japan Patent Office on Sep. 30, 2022, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

The invention claimed is:

1. A snow accretion test method comprising:
a snow accumulation step of accumulating snow on a specimen; and
a snow accretion step of freezing snow accumulated on the specimen in a state where snow is not supplied to the specimen, the snow accretion step at least including a period in which an ambient temperature of the specimen is adjusted to a negative temperature,
wherein in the snow accretion step, an ambient temperature of the specimen is adjusted to a temperature lower than an ambient temperature in the snow accumulation step.

2. The snow accretion test method according to claim 1, wherein the snow accumulation step and the snow accretion step are repeatedly performed.

3. The snow accretion test method according to claim 1 comprising a snow drop step of raising an ambient temperature of the specimen or a specimen temperature so that snow accumulated on the specimen drops from the specimen.

4. A snow accretion test method comprising:
a snow accumulation step of accumulating snow on a specimen;
a snow melting step of melting snow accumulated on the specimen in the snow accumulation step so that wet snow is accumulated on the specimen; and
a snow accretion step of freezing the snow accumulated on the specimen in the snow accumulation step and melted in the snow melting step in a state where snow is not supplied to the specimen, the snow accretion step including a period in which an ambient temperature of the specimen is adjusted to a negative temperature.

5. A snow accretion test device comprising:
a test chamber configured for providing a snowfall environment;
an air conditioner configured for air-conditioning an inside of the test chamber;
a nozzle configured for spraying water particles for obtaining the snowfall environment in the test chamber; and
a controller configured to control the air conditioner and the nozzle, wherein
the controller is configured to perform a snow accumulation step of accumulating snow on a specimen by controlling the air conditioner and the nozzle so that a temperature in the test chamber becomes a temperature set as a temperature for the snow accumulation step and snow accumulates on the specimen,
the controller is configured to perform a snow accretion step of freezing snow accumulated on the specimen after the snow accumulation step by controlling the air conditioner and the nozzle so that the temperature in the test chamber becomes a temperature set as a temperature for the snow accretion step and the snow accretion step includes a period in which an ambient temperature of the specimen is adjusted to a negative temperature so as to freeze the snow accumulated on the specimen in a state that snow is not supplied to the specimen, and in the snow accretion step, the controller controls the air conditioner so that an ambient temperature of the specimen is adjusted to a temperature lower than an ambient temperature in the snow accumulation step.

6. The snow accretion test device according to claim 5, wherein the controller is configured to control the air conditioner and the nozzle so that the snow accumulation step and the snow accretion step are repeatedly performed.

7. The snow accretion test device according to claim 5, wherein the controller is configured to control the air conditioner so that a snow drop step of raising an ambient temperature of the specimen or a specimen temperature is performed so that snow accumulated on the specimen drops from the specimen.

8. A snow accretion test device comprising:

a test chamber configured for providing a snowfall environment;

an air conditioner configured for air-conditioning an inside of the test chamber;

a nozzle configured for spraying water particles for obtaining the snowfall environment in the test chamber; and a controller configured to control the nozzle and the air conditioner, wherein the controller is configured to perform a snow accumulation step by controlling the air conditioner and the nozzle so that a temperature in the test chamber becomes a temperature set as a temperature for the snow accumulation step and snow accumulates on a specimen, the controller is configured to perform a snow melting step by controlling the air conditioner so that snow accumulated on the specimen in the snow accumulation step melts and wet snow is accumulated on the specimen, and the controller is configured to perform a snow accretion step by controlling the air conditioner and the nozzle so that the temperature in the test chamber becomes a temperature set as a temperature for the snow accretion step and the snow accretion step includes a period in which an ambient temperature of the specimen is adjusted to a negative temperature to freeze the snow accumulated on the specimen in the snow accumulation step and melted in the snow melting step in a state where snow is not supplied to the specimen.

* * * * *